US00RE37381B1

(19) United States
(12) Reissued Patent
Purcell et al.

(10) Patent Number: US RE37,381 E
(45) Date of Reissued Patent: Sep. 18, 2001

(54) VACCINE AGAINST HEPATITIS A VIRUS

(75) Inventors: Robert H. Purcell, Boyds; John R. Ticehurst, Kensington; Jeffrey I. Cohen, Silver Spring; Suzanne U. Emerson, Rockville, all of MD (US); Stephen M. Feinstone, Washington, DC (US); Richard J. Daemer, Kensington, MD (US); Ian D. Gust, Ivanhoe (AU)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

(21) Appl. No.: 08/673,408

(22) Filed: Sep. 6, 1995

Related U.S. Patent Documents

Reissue of:

(64) Patent No.: 4,894,228
Issued: Jan. 16, 1990
Appl. No.: 07/217,824
Filed: Jul. 12, 1988

U.S. Applications:

(63) Continuation of application No. 07/822,639, filed on Jan. 16, 1992, now abandoned, which is a continuation-in-part of application No. 06/905,146, filed on Sep. 9, 1986, now abandoned, which is a continuation-in-part of application No. 06/652,067, filed on Sep. 19, 1984, now Pat. No. 4,620,978, which is a continuation-in-part of application No. 06/366,165, filed on Apr. 7, 1982, now Pat. No. 4,532,215.

(51) Int. Cl.[7] ..... A61K 39/29; C12N 7/08; C07H 21/04

(52) U.S. Cl. ..... 424/226.1; 435/235.1; 435/237; 536/23.72

(58) Field of Search ..... 424/226.1; 536/23.72; 435/237, 235.1

(56) References Cited

U.S. PATENT DOCUMENTS 4,164,566 * 8/1979 Provost et al. ..... 424/89
4,620,978 * 11/1986 Daemer et al. ..... 424/226.1

OTHER PUBLICATIONS

Cohen et al., "Complete Nucleotide Sequence . . . ," Proc Natl Acad Sci (USA) 84:2497–2501 (1987).*

Cohen et al., "Complete Nucleotide Sequence . . . ," J Virol. 61:50–59 (1987).*

Ticehurst et al., "Molecular Cloning and Characterization . . . ," Proc Natl Acad Sci (USA) 80:5885–89 (1983).*

Feinstone, S. M., Daemer, R. J., Gust, I. D., Purcell, R. H., Live Attenuated Vaccine for Hepatitis A, Dev. Biol. Stand., 1983; 54: 429–432.*

Provost, P. J., Conti, P. A., Giesa, P. A. et al., Studies in Chimpanzees of Live, Attenuated Hepatitis A Vaccine Candidates, Proc. Soc. Exp. Biol. Med., 1983; 172: 357–363.*

Ticehurst, J. R., Racaniello, V. R., Baroudy, B. M., Baltimore, D., Purcell, R. H., Feinstone, S. M., Molecular Cloning and Characterization of Hepatitis A Virus cDNA, Proc. Natl. Acad. Sci. USA, 1983; 80: 5885–5889.* von der Helm, K., Winnacker, E. L., Deinhardt, F. et al., Cloning of Hepatitis A Virus Genome, J. Virol. Methods, 1981; 3: 37–43.*

Daemer et al., Infection and Immunity, 32(1): 388–393, Apr. 1981.*

Purcell et al., "Hepatitis A Virus" (in press).*

* cited by examiner

*Primary Examiner*—Michael P. Woodward
(74) *Attorney, Agent, or Firm*—Morgan & Finnegan, LLP

(57) ABSTRACT

The present invention provides an attenuated hepatitis A virus useful as a vaccine.

24 Claims, 12 Drawing Sheets

Figure 2:
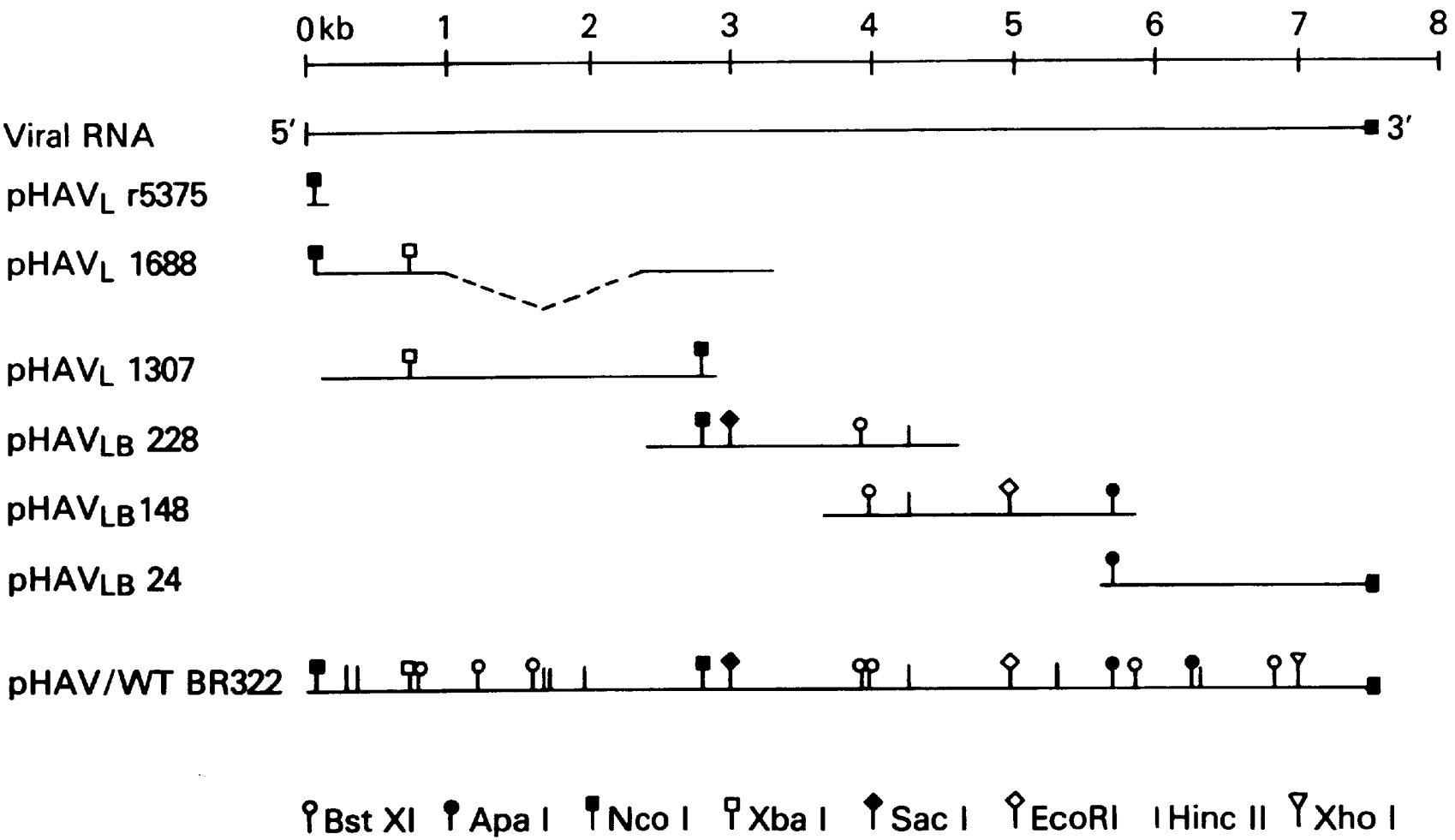

```
                                                  50                                                  100
TTCAAGAGGGGTCTCCGGGAATTTCCGGAGTCCCTCTTGGAAGTCCATGGTGAGGGGACTTGATACCTCACCGCCGTTTGCCTAGGCTATAGGCTAAATTTTCCCTTTCCCTTTTCCCTTTC

                          150                                                 200
CTATTCCCTTTGTTTTGCTTGTAAATATTAATTCCTGCAGGTTCAGGGTTCTTAAATCTGTTTCTCTATAAGAACACTCATTTTTCACGCTTTCTGTCTTCTTTCTTCCAGGGCTCTCCC

     250                                                 300                                                 350
CTTGCCCTAGGCTCTGGCCGTTGCGCCCGGCGGGGTCAACTCCATGATTAGCATGGAGCTGTAGGAGTCTAAATTGGGGACACAGATGTTTGGAACGTCACCTTGCAGTGTTAACTTGGC

                                  400                                                 450
TTTCATGAATCTCTTTGATCTTCCACAAGGGGTAGGCTACGGGTGAAACCTCTTAGGCTAATACTTCTATGAAGAGATGCCTTGGATAGGGTAACAGCGGCGGATATTGGTGAGTTGTTA

                500                                                 550                                                 600
AGACAAAAACCATTCAACGCCGGAGGACTGACTCTCATCCAGTGGATGCATTGAGTGGATTGACTGTCAGGGCTGTCTTTAGGCTTAATTCCAGACCTCTCTGTGCTTAGGGCAAACATC

                                                  650                                                 700
ATTTGGCCTTAAATGGGATTCTGTGAGAGGGGATCCCTCCATTGACAGCTGGACTGTTCTTTGGGGCCTTATGTGGTGTTTGCCTCTGAGGTACTCAGGGGCATTTAGGTTTTTCCTCAT

     730    < VP4 = 1A (nt 735-803 / aa 1-23 / 23 aa)                    VP4 >< VP2 = 1B (nt 804-1469 / aa 24-245 /
TCTTAAATAATAATGAACATGTCTAGACAAGGTATTTTCCAGACTGTTGGGAGTGGTCTTGACCACATCCTGTCTTTGGCAGACATTGAGGAAGAGCAAATGATTCAATCAGTTGATAGG
             M  N  M  S  R  Q  G  I  F  Q  T  V  G  S  G  L  D  H  I  L  S  L  A  D  I  E  E  E  Q  M  I  Q  S  V  D  R

 222 aa)                                                 900                                                 950
ACTGCAGTGACTGGTGCTTCTTATTTTACTTCTGTGGATCAATCTTCAGTTCATACAGCTGAGGTTGGATCACACCAGGTTGAACCTTTGAGAACCTCTGTTGATAAACCCGGTTCAAAG
 T  A  V  T  G  A  S  Y  F  T  S  V  D  Q  S  S  V  H  T  A  E  V  G  S  H  Q  V  E  P  L  R  T  S  V  D  K  P  G  S  K

                                  1000                                                1050
AAGACTCAGGGAGAGAAATTTTTCTTGATTCATTCTGCAGATTGGCTTACTACACATGCTCTTTTCCATGAAGTTGCAAAATTGGATGTGGTGAAATTATTATACAATGAGCAGTTTGCT
 K  T  Q  G  E  K  F  F  L  I  H  S  A  D  W  L  T  T  H  A  L  F  H  E  V  A  K  L  D  V  V  K  L  L  Y  N  E  Q  F  A
```

FIG. 1A

```
                1100                                                1150                                                1200
GTTCAAGGGTTGTTGAGATACCATACATATGCAAGATTTGGCATTGAAATTCAAGTTCAGATAAACCCTACACCTTTCCAACAGGGGGGATTGATCTGTGCTATGGTTCCTGGTGACCAG
 V  Q  G  L  L  R  Y  H  T  Y  A  R  F  G  I  E  I  Q  V  Q  I  N  P  T  P  F  Q  Q  G  G  L  I  C  A  M  V  P  G  D  Q

                                                    1250                                                1300
AGCTATGGTTCTATAGCATCATTGACTGTTTATCCTCATGGTTTGTTAAATTGCAATATTAACAATGTGGTTAGAATAAAGGTTCCATTTATTTACACAAGAGGTGCTTACCACTTTAAA
 S  Y  G  S  I  A  S  L  T  V  Y  P  H  G  L  L  N  C  N  I  N  N  V  V  R  I  K  V  P  F  I  Y  T  R  G  A  Y  H  F  K

                        1350                                                1400
GATCCACAATACCCAGTTTGGGAATTGACAATTAGAGTTTGGTCAGAATTAAATATTGGGACAGGAACTTCAGCTTATACTTCACTCAATGTTTTAGCTAGATTTACAGATTTGGAGTTG
 D  P  Q  Y  P  V  W  E  L  T  I  R  V  W  S  E  L  N  I  G  T  G  T  S  A  Y  T  S  L  N  V  L  A  R  F  T  D  L  E  L

   1450                VP2 >< VP3 = 1C (nt 1470-2207 / aa 246-491 / 246 aa)                                          1550
CATGGATTAACTCCTCTTTCTACACAAATGATGAGAAATGAATTTAGGGTCAGTACTACTGAGAATGTGGTGAATCTGTCAAATTATGAAGATGCAAGAGCAAAGATGTCTTTTGCTTTG
 H  G  L  T  P  L  S  T  Q  M  M  R  N  E  F  R  V  S  T  T  E  N  V  V  N  L  S  N  Y  E  D  A  R  A  K  M  S  F  A  L

                                    1600                                                1650
GATCAGGAAGATTGGAAATCTGATCCGTCCCAGGGTGGTGGGATCAAAATTACTCATTTTACTACTTGGACATCTATTCCAACTTTGGCTGCTCAGTTTCCATTTAATGCTTCAGACTCA
 D  Q  E  D  W  K  S  D  P  S  Q  G  G  G  I  K  I  T  H  F  T  T  W  T  S  I  P  T  L  A  A  Q  F  P  F  N  A  S  D  S

                1700                                                1750                                                1800
GTTGGTCAACAAATTAAAGTTATTCCAGTTGACCCATATTTTTTCCAAATGACAAATACGAATCCTGACCAAAAATGTATAACTGCTTTGGCTTCTATTTGTCAGATGTTTTGTTTTTGG
 V  G  Q  Q  I  K  V  I  P  V  D  P  Y  F  F  Q  M  T  N  T  N  P  D  Q  K  C  I  T  A  L  A  S  I  C  Q  M  F  C  F  W

                                                    1850                                                1900
AGAGGAGATCTTGTCTTTGATTTTCAAGTTTTTCCCACCAAATATCATTCAGGTAGATTACTGTTTTGTTTTGTTCCTGGCAATGAGCTAATAGATGTTTCTGGAATCACATTAAAGCAA
 R  G  D  L  V  F  D  F  Q  V  F  P  T  K  Y  H  S  G  R  L  L  F  C  F  V  P  G  N  E  L  I  D  V  S  G  I  T  L  K  Q
```

FIG.1B

```
                                1950                                                    2000
GCAACTACTGCTCCTTGTGCAGTAATGGATATTACAGGAGTGCAGTCAACTTTGAGATTTCGTGTTCCCTGGATTTCTGACACTCCTTACAGAGTGAACAGGTATACAAAGTCAGCACAT
 A  T  T  A  P  C  A  V  M  D  I  T  G  V  Q  S  T  L  R  F  R  V  P  W  I  S  D  T  P  Y  R  V  N  R  Y  T  K  S  A  H

    2050                                                2100                                                    2150
CAGAAAGGTGAGTACACTGCCATTGGGAAGCTTATTGTGTATTGTTATAACAGATTGACCTCTCCTTCTAACGTTGCTTCCCATGTCAGAGTGAATGTTTATCTTTCAGCAATTAACTTG
 Q  K  G  E  Y  T  A  I  G  K  L  I  V  Y  C  Y  N  R  L  T  S  P  S  N  V  A  S  H  V  R  V  N  V  Y  L  S  A  I  N  L

                                        2200  VP3 >< VP1 = 1D (nt 2208-3107 / aa 492-791 / 300 aa)
GAATGTTTTGCTCCTCTTTATCATGCTATGGATGTTACTACACAAGTTGGAGATGATTCTGGAGGTTTTTCAACAACAGTTTCTACAGAACAGAATGTTCCAGATCCCCAAGTTGGTATA
 E  C  F  A  P  L  Y  H  A  M  D  V  T  T  Q  V  G  D  D  S  G  G  F  S  T  T  V  S  T  E  Q  N  V  P  D  P  Q  V  G  I

                2300                                                    2350                                                    2400
ACAACCATGAAAGATTTGAAAGGAAAAGCTAACAGAGGGAAAATGGATGTTTCAGGAGTACAAGCACCTGTGGGAGCTATCACAACAATTGAGGATCCAGTTTTAGCAAAGAAAGTACCT
 T  T  M  K  D  L  K  G  K  A  N  R  G  K  M  D  V  S  G  V  Q  A  P  V  G  A  I  T  T  I  E  D  P  V  L  A  K  K  V  P

                                            2450                                                    2500
GAGACATTTCCTGAATTGAAACCTGGAGAATCCAGACATACATCAGATCATATGTCCATCTACAAGTTTATGGGAAGGTCTCATTTCTTGTGCACTTTTACATTCAATTCAAATAATAAA
 E  T  F  P  E  L  K  P  G  E  S  R  H  T  S  D  H  M  S  I  Y  K  F  M  G  R  S  H  F  L  C  T  F  T  F  N  S  N  N  K

                        2550                                                    2600
GAGTACACATTTCCTATAACCTTGTCTTCAACCTCTAATCCTCCTCATGGTTTGCCATCAACACTGAGGTGGTTTTTCAACTTGTTTCAGTTGTATAGAGGGCCTTTAGATCTGACAATT
 E  Y  T  F  P  I  T  L  S  S  T  S  N  P  P  H  G  L  P  S  T  L  R  W  F  F  N  L  F  Q  L  Y  R  G  P  L  D  L  T  I

    2650                                                2700                                                    2750
ATTATTACAGGAGCAACTGATGTAGATGGCATGGCCTGGTTCACTCCAGTAGGTCTTGCCGTTGATACTCCTTGGGTAGAGAAGGAGTCAGCTTTGTCTATTGACTACAAAACTGCTCTT
 I  I  T  G  A  T  D  V  D  G  M  A  W  F  T  P  V  G  L  A  V  D  T  P  W  V  E  K  E  S  A  L  S  I  D  Y  K  T  A  L
```

FIG.1C

```
                                   2800                                                  2850
GGAGCTGTCAGATTTAACACAAGGAGAACAGGGAACATTCAGATTAGATTACCATGGTATTCTTATTTATATGCTGTGTCTGGAGCACTGGATGGTTTGGGTGACAAGACAGATTCTACA
 G  A  V  R  F  N  T  R  R  T  G  N  I  Q  I  R  L  P  W  Y  S  Y  L  Y  A  V  S  G  A  L  D  G  L  G  D  K  T  D  S  T

            2900                                                 2950                                                 3000
TTTGGATTGGTTTCTATTCAGATTGCAAATTACAATCATTCTGATGAATACTTGTCTTTTAGTTGTTATTTGTCTGTCACAGAACAATCAGAGTTTTATTTTCCCAGAGCTCCATTGAAC
 F  G  L  V  S  I  Q  I  A  N  Y  N  H  S  D  E  Y  L  S  F  S  C  Y  L  S  V  T  E  Q  S  E  F  Y  F  P  R  A  P  L  N

                                          3050                                                 3100  VP1 >< 2A
TCAAATGCCATGTTATCCACTGAATCAATGATGAGCAGAATTGCAGCTGGAGACTTGGAGTCATCAGTGGATGATCCTAGATCAGAGGAAGATAAAAGATTTGAGAGTCATATAGAATGC
 S  N  A  M  L  S  T  E  S  M  M  S  R  I  A  A  G  D  L  E  S  S  V  D  D  P  R  S  E  E  D  K  R  F  E  S  H  I  E  C

 (nt 3108-3674 / aa 792-980 / 189 aa)                                   3200
AGGAAGCCATATAAAGAACTGAGATTAGAAGTTGGGAAACAAAGACTCAAGTATGCTCAGGAAGAATTGTCAAATGAAGTACTTCCACCCCCTAGGAAAATGAAGGGACTGTTTTCACAA
 R  K  P  Y  K  E  L  R  L  E  V  G  K  Q  R  L  K  Y  A  Q  E  E  L  S  N  E  V  L  P  P  P  R  K  M  K  G  L  F  S  Q

   3250                                                 3300                                                 3350
GCCAAAATTTCTCTTTTTTATACTGAGGAGCATGAAATAATGAAGTTTTCCTGGAGAGGTGTGACTGCTGATACTAGAGCTTTAAGGAGGTTTGGATTCTCTTTGGCCGCAGGCAGAAGT
 A  K  I  S  L  F  Y  T  E  E  H  E  I  M  K  F  S  W  R  G  V  T  A  D  T  R  A  L  R  R  F  G  F  S  L  A  A  G  R  S

                                   3400                                                  3450
GTGTGGACTCTTGAAATGGATGCTGGGGTTCTTACTGGGAGACTGATTAGATTGAATGATGAGAAATGGACAGAAATGAAGGATGACAAGATTGTTTCATTGATTGAAAAGTTTACAAGT
 V  W  T  L  E  M  D  A  G  V  L  T  G  R  L  I  R  L  N  D  E  K  W  T  E  M  K  D  D  K  I  V  S  L  I  E  K  F  T  S

            3500                                                 3550                                                 3600
AACAAATATTGGTCCAAAGTGAATTTCCCACATGGGATGTTGGATCTTGAAGAAATTGCTGCCAATTCTAAGGATTTTCCTAACATGTCTGAAACGGATTTGTGTTTCTTGCTGCATTGG
 N  K  Y  W  S  K  V  N  F  P  H  G  M  L  D  L  E  E  I  A  A  N  S  K  D  F  P  N  M  S  E  T  D  L  C  F  L  L  H  W
```

FIG.1D

```
                                                 3650                  2A >< 2B (nt 3675-3995 / aa 981-1087 / 107 aa)
TTAAATCCAAAGAAAATTAATTTAGCAGATAGAATGCTTGGATTGTCTGGAGTTCAGGAAATTAAAGAACAAGGTGTTGGATTAATAGCAGAGTGTAGAACTTTCTTAGATTCTATTGCT
 L  N  P  K  K  I  N  L  A  D  R  M  L  G  L  S  G  V  Q  E  I  K  E  Q  G  V  G  L  I  A  E  C  R  T  F  L  D  S  I  A

                         3750                                                    3800
GGAACTTTAAAATCTATGATGTTTGGATTTCATCATTCTGTGACTGTTGAAATTATAAACACTGTGCTCTGTTTTGTTAAGAGTGGAATTTTGCTTTATGTAATACAACAATTGAATCAG
 G  T  L  K  S  M  M  F  G  F  H  H  S  V  T  V  E  I  I  N  T  V  L  C  F  V  K  S  G  I  L  L  Y  V  I  Q  Q  L  N  Q

   3850                                                   3900                                                   3950
GATGAACATTCTCACATAATTGGTTTGTTGAGAGTCATGAATTATGCAGATATTGGTTGTTCAGTTATTTCATGTGGCAAAGTTTTTTCCAAAATGCTGGAAACAGTCTTTAATTGGCAA
 D  E  H  S  H  I  I  G  L  L  R  V  M  N  Y  A  D  I  G  C  S  V  I  S  C  G  K  V  F  S  K  M  L  E  T  V  F  N  W  Q

                                 2B >< 2C (nt 3996-5000 / aa 1088-1422 / 335 aa)          4050
ATGGACTCCAGAATGATGGAGTTAAGGACTCAGAGTTTTTCCAACTGGTTAAGAGATATTTGTTCTGGGATCACCATTTTTAAAAACTTCAAGGATGCAATTTATTGGCTTTATACAAAA
 M  D  S  R  M  M  E  L  R  T  Q  S  F  S  N  W  L  R  D  I  C  S  G  I  T  I  F  K  N  F  K  D  A  I  Y  W  L  Y  T  K

              4100                                                   4150                                                   4200
TTAAAGGACTTTTATGAAGTGAATTATGGCAAGAAGAAGGACATTTTAAATATTCTTAAAGATAACCAACAAAAAATAGAGAAAGCCATTGAGGAAGCCGATGAATTTTGCATTTTGCAA
 L  K  D  F  Y  E  V  N  Y  G  K  K  K  D  I  L  N  I  L  K  D  N  Q  Q  K  I  E  K  A  I  E  E  A  D  E  F  C  I  L  Q

                                                 4250                                                   4300
ATCCAAGATGTGGAAAAATTTGAACAGTATCAGAAAGGGGTTGACTTGATACAAAAATTGAGAACTGTTCATTCAATGGCTCAGGTTGATCCAAATTTAATGGTTCATTTGTCACCTTTG
 I  Q  D  V  E  K  F  E  Q  Y  Q  K  G  V  D  L  I  Q  K  L  R  T  V  H  S  M  A  Q  V  D  P  N  L  M  V  H  L  S  P  L

                         4350                                                    4400
AGAGATTGTATAGCAAGAGTTCATCAGAAACTTAAAAACCTTGGATCTATAAATCAGGCAATGGTAACGAGATGTGAGCCAGTTGTTTGTTATTTATATGGCAAAAGAGGGGGAGGAAAG
 R  D  C  I  A  R  V  H  Q  K  L  K  N  L  G  S  I  N  Q  A  M  V  T  R  C  E  P  V  V  C  Y  L  Y  G  K  R  G  G  G  K
```

FIG. 1E

```
    4450                                                4500                                                4550
AGCTTAACATCAATTGCATTGGCAACCAAAATTTGTAAACATTATGGTGTTGAGCCTGAAAAGAATATCTATACTAAACCTGTGGCTTCAGATTACTGGGATGGATATAGTGGACAATTA
 S  L  T  S  I  A  L  A  T  K  I  C  K  H  Y  G  V  E  P  E  K  N  I  Y  T  K  P  V  A  S  D  Y  W  D  G  Y  S  G  Q  L

                                  4600                                                4650
GTTTGCATCATTGATGATATTGGCCAAAACACAACAGATGAGGATTGGTCAGATTTTTGTCAGTTAGTGTCAGGATGTCCAATGAGATTAAACATGGCCTCTCTTGAGGAGAAGGGTAGG
 V  C  I  I  D  D  I  G  Q  N  T  T  D  E  D  W  S  D  F  C  Q  L  V  S  G  C  P  M  R  L  N  M  A  S  L  E  E  K  G  R

             4700                                                4750                                                4800
CATTTTTCTTCTCCTTTTATAATAGCAACTTCAAATTGGTCAAATCCAAGTCCAAAAACAGTTTATGTTAAGGAAGCAATTGACCGCAGACTCCATTTCAAGGTTGAAGTTAAACCTGCT
 H  F  S  S  P  F  I  I  A  T  S  N  W  S  N  P  S  P •K  T  V  Y  V  K  E  A  I  D  R  R  L  H  F  K  V  E  V  K  P  A

                                          4850                                                4900
TCATTTTTCAAAAATCCTCACAATGATATGTTGAATGTTAATTTAGCTAAAACAAATGATGCAATCAAAGATATGTCTTGTGTTGATTTGATAATGGATGGACATAATGTTTCATTGATG
 S  F  F  K  N  P  H  N  D  M  L  N  V  N  L  A  K  T  N  D  A  I  K  D  M  S  C  V  D  L  I  M  D  G  H  N  V  S  L  M

                       4950                                                2C >< 3A (nt 5001-5222 / aa 1423-1496 / 74 aa)
GATTTGCTCAGTTCTTTAGTCATGACAGTTGAAATTAGAAAACAAAACATGACTGAATTCATGGAGTTGTGGTCTCAGGGAATTTCAGATGATGATAATGATAGTGCAGTAGCTGAGTTT
 D  L  L  S  S  L  V  M  T  V  E  I  R  K  Q  N  M  T  E  F  M  E  L  W  S  Q  G  I  S  D  D  D  N  D  S  A  V  A  E  F

    5050                                                5100                                                5150
TTCCAGTCTTTTCCATCTGGTGAACCATCGAACTCTAAATTATCTGGCTTTTTCCAATCTGTTACTAATCACAAGTGGGTTGCTGTGGGAGCTGCAGTTGGCATTCTTGGAGTGCTCGTT
 F  Q  S  F  P  S  G  E  P  S  N  S  K  L  S  G  F  F  Q  S  V  T  N  H  K  W  V  A  V  G  A  A  V  G  I  L  G  V  L  V

                                  5200                 3A >< 3B = VPg (nt 5223-5291 / aa 1497-1519 / 23 aa)
GGAGGATGGTTTGTGTATAAGCATTTCTCCCGCAAAGAGGAGGAACCAATCCCAGCTGAAGGGGTATATCATGGTGTAACTAAGCCCAAGCAAGTGATTAAATTAGATGCAGATCCAGTA
 G  G  W  F  V  Y  K  H  F  S  R  K  E  E  E  P  I  P  A  E  G  V  Y  H  G  V  T  K  P  K  Q  V  I  K  L  D  A  D  P  V
```

FIG.1F

```
     3B >< 3C (nt 5292-5948 / aa 1520-1738 / 219 aa)          5350                                                  5400
GAATCTCAGTCAACTTTGGAAATAGCAGGACTGGTTAGGAAGAACTTGGTTCAGTTTGGAGTTGGAGAGAAGAATGGATGTGTGAGATGGGTTATGAATGCCTTGGGAGTGAAAGATGAT
 E  S  Q  S  T  L  E  I  A  G  L  V  R  K  N  L  V  Q  F  G  V  G  E  K  N  G  C  V  R  W  V  M  N  A  L  G  V  K  D  D

                                                 5450                                                  5500
TGGCTGCTTGTGCCTTCCCATGCTTATAAATTTGAGAAAGATTATGAAATGATGGAGTTTTATTTTAATAGAGGTGGAACTTACTATTCAATTTCAGCTGGTAATGTTGTTATTCAATCT
 W  L  L  V  P  S  H  A  Y  K  F  E  K  D  Y  E  M  M  E  F  Y  F  N  R  G  G  T  Y  Y  S  I  S  A  G  N  V  V  I  Q  S

                         5550                                                  5600
TTGGATGTGGGATTCCAGGATGTTGTTCTGATGAAGGTTCCTACAATTCCTAAGTTTAGAGATATTACTCAGCATTTTATTAAGAAAGGGGATGTGCCTAGAGCTTTGAATCGCCTGGCA
 L  D  V  G  F  Q  D  V  V  L  M  K  V  P  T  I  P  K  F  R  D  I  T  Q  H  F  I  K  K  G  D  V  P  R  A  L  N  R  L  A

    5650                                                 5700                                                  5750
ACATTAGTGACAACTGTAAATGGAACCCCTATGTTAATTTCTGAGGGCCCACTAAAGATGGAAGAGAAAGCTACTTATGTTCATAAGAAAAATGATGGTACAACAGTTGATTTAACTGTG
 T  L  V  T  T  V  N  G  T  P  M  L  I  S  E  G  P  L  K  M  E  E  K  A  T  Y  V  H  K  K  N  D  G  T  T  V  D  L  T  V

                                  5800                                                  5850
GATCAGGCATGGAGAGGAAAAGGCGAAGGTCTTCCTGGAATGTGTGGTGGGGCCTTGGTTTCATCGAATCAATCTATACAGAATGCAATCTTGGGCATCCATGTTGCTGGAGGAAATTCA
 D  Q  A  W  R  G  K  G  E  G  L  P  G  M  C  G  G  A  L  V  S  S  N  Q  S  I  Q  N  A  I  L  G  I  H  V  A  G  G  N  S

             5900                                                 3C >< 3D (nt 5949-7415 / aa 1739-2227 / 489 aa)     6000
ATTCTTGTTGCAAAATTGGTTACTCAAGAAATGTTCCAAAATATTGATAAGAAAATTGAAAGTCAGAGAATTATGAAAGTGGAGTTTACTCAGTGTTCAATGAATGTGGTCTCCAAAACG
 I  L  V  A  K  L  V  T  Q  E  M  F  Q  N  I  D  K  K  I  E  S  Q  R  I  M  K  V  E  F  T  Q  C  S  M  N  V  V  S  K  T

                                                 6050                                                  6100
CTTTTTAGAAAGAGTCCCATTTATCATCACATTGATAAAACCATGATTAATTTTCCTGCAGCTATGCCCTTTTCTAAAGCTGAAATTGATCCAATGGCTGTGATGTTATCTAAGTATTCA
 L  F  R  K  S  P  I  Y  H  H  I  D  K  T  M  I  N  F  P  A  A  M  P  F  S  K  A  E  I  D  P  M  A  V  M  L  S  K  Y  S
```

FIG. 1G

```
                                6150                                                    6200
TTACCTATTGTAGAAGAACCAGAGGATTATAAAGAGGCTTCAATTTTTTATCAAAATAAAATAGTGGGTAAGACTCAGTTAGTTGATGATTTTTTAGATCTTGATATGGCCATTACAGGG
 L  P  I  V  E  E  P  E  D  Y  K  E  A  S  I  F  Y  Q  N  K  I  V  G  K  T  Q  L  V  D  D  F  L  D  L  D  M  A  I  T  G

    6250                                                    6300                                                    6350
GCCCCAGGAATTGATGCTATCAACATGGATTCATCTCCTGGATTTCCTTATGTCCAGGAGAAGTTGACCAAAAGAGATTTAATTTGGTTGGATGAAAATGGTTTATTGCTGGGAGTTCAT
 A  P  G  I  D  A  I  N  M  D  S  S  P  G  F  P  Y  V  Q  E  K  L  T  K  R  D  L  I  W  L  D  E  N  G  L  L  L  G  V  H

                                6400                                                    6450
CCAAGATTGGCTCAGAGAATCTTATTCAATACTGTCATGATGGAAAATTGTTCTGATTTGGATGTTGTTTTTACAACCTGTCCAAAAGATGAATTGAGACCATTAGAGAAAGTGTTGGAA
 P  R  L  A  Q  R  I  L  F  N  T  V  M  M  E  N  C  S  D  L  D  V  V  F  T  T  C  P  K  D  E  L  R  P  L  E  K  V  L  E

                6500                                                    6550                                                    6600
TCAAAAACAAGAGCTATTGATGCTTGTCCTCTGGATTACTCAATTTTGTGCCGAATGTATTGGGGTCCAGCTATTAGTTATTTTCATTTGAATCCAGGTTTCCATACAGGTGTTGCTATT
 S  K  T  R  A  I  D  A  C  P  L  D  Y  S  I  L  C  R  M  Y  W  G  P  A  I  S  Y  F  H  L  N  P  G  F  H  T  G  V  A  I

                                6650                                                    6700
GGCATAGATCCTGATAGACAGTGGGATGAATTATTTAAAACAATGATAAGATTCGGAGATGTTGGTCTTGATTTAGATTTCTCTGCTTTTGATGCTAGTCTTAGTCCATTTATGATTAGA
 G  I  D  P  D  R  Q  W  D  E  L  F  K  T  M  I  R  F  G  D  V  G  L  D  L  D  F  S  A  F  D  A  S  L  S  P  F  M  I  R

                                6750                                                    6800
GAAGCAGGTAGAATCATGAGTGAACTATCTGGAACTCCATCCCATTTTGGCACAGCTCTTATCAATACTATCATTTATTCCAAGCATTTGCTGTATAACTGTTGTTACCATGTCTGTGGT
 E  A  G  R  I  M  S  E  L  S  G  T  P  S  H  F  G  T  A  L  I  N  T  I  I  Y  S  K  H  L  L  Y  N  C  C  Y  H  V  C  G

    6850                                                    6900                                                    6950
TCAATGCCCTCTGGGTCTCCTTGTACAGCTTTGCTAAATTCAATTATTAATAATGTCAATTTGTATTATGTGTTTTCCAAGATATTTGGAAAGTCTCCAGTTTTCTTTTGTCAGGCTTTG
 S  M  P  S  G  S  P  C  T  A  L  L  N  S  I  I  N  N  V  N  L  Y  Y  V  F  S  K  I  F  G  K  S  P  V  F  F  C  Q  A  L
```

FIG.1H

```
                                    7000                                                    7050
AAGATTCTCTGTTATGGAGATGATGTTTTAATAGTTTTCTCTCGAGATGTTCAGATTGATAATCTTGATTTGATTGGACAAAAAATTGTAGATGAGTTTAAGAAACTTGGCATGACAGCT
 K  I  L  C  Y  G  D  D  V  L  I  V  F  S  R  D  V  Q  I  D  N  L  D  L  I  G  Q  K  I  V  D  E  F  K  K  L  G  M  T  A

            7100                                                    7150                                                    7200
ACTTCTGCTGACAAGAATGTACCTCAGCTGAAACCAGTTTCGGAATTGACTTTTCTCAAAAGATCTTTCAATTTGGTAGAGGATAGAATTAGACCTGCAATTTCGGAAAAAACAATTTGG
 T  S  A  D  K  N  V  P  Q  L  K  P  V  S  E  L  T  F  L  K  R  S  F  N  L  V  E  D  R  I  R  P  A  I  S  E  K  T  I  W

                                                 7250                                                    7300
TCTTTAATAGCATGGCAGAGAAGTAACGCTGAGTTTGAGCAGAATTTAGAAAATGCTCAGTGGTTTGCTTTTATGCATGGCTATGAGTTTTATCAGAAATTTTATTATTTTGTTCAGTCC
 S  L  I  A  W  Q  R  S  N  A  E  F  E  Q  N  L  E  N  A  Q  W  F  A  F  M  H  G  Y  E  F  Y  Q  K  F  Y  Y  F  V  Q  S

                        7350                                                    7400          3D >
TGTTTGGAGAAAGAGATGATAGAATACAGACTTAAATCTTATGATTGGTGGAGAATGAGATTTTATGACCAGTGTTTCATTTGTGACCTTTCATGATTTGTTTAAACAAATTTTCTTAAA
 C  L  E  K  E  M  I  E  Y  R  L  K  S  Y  D  W  W  R  M  R  F  Y  D  Q  C  F  I  C  D  L  S  *        *

    7450                        7478
ATTTCTGAGGTTTGTTTATTTCTTTTATCAGTAAATAAAAAAAAAAAAAAA
```

FIG.11

VACCINE AGAINST HEPATITIS A VIRUS

Matter enclosed in heavy brackets [ ] appears in the original patent but forms no part of this reissue specification; matter printed in italics indicates the additions made by reissue.

[This application is a continuation-in-part of the application Ser. No. 905146 filed Sept. 9, 1986, now abandoned, which in turn is a continuation-in-part of Ser. No. 652,067 filed Sept. 19, 1984, now U.S. Pat. No. 4,620,978, issued Nov. 4, 1986.] *This is a continuation of co-pending application Ser. No. 07/822,639, filed on Jan. 16, 1992, abandoned; which is a reissue application of U.S. Pat. No. 4,894,228 issued Jan. 16, 1990, of Ser. No. 07/217,824, filed Jul. 12, 1988; which is a Continuation-In-Part of Ser. No. 06/905,146, filed Sep. 9, 1986 now abandoned; which is a Continuation-In-Part of Ser. No. 06/652,067, filed Sep. 19, 1984, now U.S. Pat. No. 4,620,978 issued Nov. 4, 1986; which is a Continuation-In-Part of Ser. No. 06/366,165, filed Apr. 7, 1982, now U.S. Pat. No. 4,532,215 issued Jul. 30, 1985.*

SUMMARY OF THE INVENTION

The present invention provides complete nucleotide sequence of attenuated hepatitis A virus, HAV strain HM-175 Pass 35, which is significantly different from wild-type HAV. This new strain of HAV differs from wild-type HAV HM-175 by several nucleotide changes distributed throughout the genome, is attenuated for chimpanzees, elicits serum neutralizing antibodies, and is suitable for use as an HAV vaccine. It is noted, however, that not all the changes in HM-175 Pass 35 are necessary for attenuation and use as a vaccine. The attenuated virus of the present invention grows well in cell culture. [the] *The* invention describes those mutations that are involved in cell culture adaptation and attenuation.

BACKGROUND OF THE INVENTION

Hepatitis A virus (HAV) is responsible for over 20,000 cases of hepatitis in the United States each year. Certain populations are at high risk for infection with HAV including foreign travelers, children attending day care centers and their close contacts, military personnel, and persons with close contact of patients with hepatitis A. Currently, passive immunization with immune serum globulin (ISG) is the only effective measure for preventing HAV infections in these patients. ISG, however, elicits only low levels of neutralizing antibody and requires repeated doses.

An effective vaccine would be useful for active immunization of populations at high risk. Inactivated HAV vaccines have been developed which are immunogenic and protective against challenge with the live virus [see Binn et al., J. Infect. Dis., 153: 749–756 (1986) and Provost et al., Proc. Soc. Exp. Biol. Med., 159: 201–203 (1978)]. These vaccines may prove effective; however, they are usually costly, may fail to produce local (or secretory) immunity, and may require repeated administration. Live HAV vaccines are under development—Provost et al. have shown that a cell culture adapted variant of HAV, strain CR-326, is attenuated (infectious, but no longer causes disease) in nonhuman primates and induces protection against challenge with wild-type (naturally occurring) virus. The experiments which constitute the parent applications of this invention disclose the development of a cell culture adapted variant of HAV, strain HM-175, which is attenuated and which elicits serum neutralizing antibody providing protection against challenge with wild-type virus in chimpanzees.

Wild-type HAV, strain HM-175, grows poorly in cell culture; however, after several passages the virus adapts to cell culture and becomes attenuated for chimpanzees [see Feinstone et al, Develop. Biol. Standard, 54: 429–432 (1983)]. The biological basis for cell culture adaptation and attenuation of HAV is unknown. The complete nucleotide sequence of the genome of wild-type (naturally occurring) HAV, strain HM-175, has been disclosed in Cohen, et al., "Complete nucleotide sequence of wild-type hepatitis A virus: comparison with different strains of hepatitis A virus and other picornaviruses." Comparison of the nucleotide sequence between wild-type HAV HM-175 and attenuated HM-175/7 indicates that a maximum of 25 nucleotide changes (resulting in 12 amino acid changes) are responsible for cell culture adaptation and attenuation of HAV-175.

While the biological basis for attenuation is unknown, three areas of the HAV genome may contain markers of attenuation. The RNAs of the 5' non-coding regions of wild-type HAV and HM-175/7 have different predicted secondary structures. The 5' non-coding region of HAV HM-175 Pass 35 has five nucleotide deletions (one 4-base and one single-base deletion) when compared to wild-type HM-175. The 5' non-coding region has the highest degree of nucleotide conservation among the different strains of HAV. However, when wild-type HM-175 and HM-175/7 are compared, 28% of the nucleotide differences (7/25 bases) are present in the 5' noncoding region, a region which contains less than 10% of the viral genome. Thus, this relatively small area of the genome may be important for both cell culture adaptation and attenuation.

The capsid region of the HAV genome may also be important for attenuation. HAV HM-175 Pass 35 has two amino acid differences from wild-type HM-175 in the capsid region. The nucleotide difference at position 3025 changes amino acid 273 of VP1 from glutamic acid (negatively charged) in wild-type HM-175 to valine (non-polar) in HM-175/7. Thus, one of the amino acid differences between wild-type and attenuated HAV HM-175 may occur at a site important for antibody binding.

The nucleotide sequences of other strains of HAV have been disclosed. A partial sequence of a variant of HAV HM-175 propagated in a cell culture not suitable for vaccine use is disclosed in Ross et al., "Molecular cloning of cDNA from hepatitis A virus strain HM-175 after multiple passages in vivo and in vitro," J. Gen. Virol. This strain was derived from wild-type virus after multiple passages (6 in vivo and 59 in vitro) and virus released into cell culture medium was used for molecular cloning. A different cell culture adapted strain of HAV (not known to be attenuated and not acceptable for vaccine production) is disclosed in Najarian et al., PNAS USA, 82: 627–631 (1985). Like HAV HM-175 Pass 35, the Ross et al variant contains a deletion of a single thymine at the nucleotide position 203–207. However, the Ross et al variant contains seven other nucleotide differences from wild-type HAV HM-175 in the 5' coding region which the variant of the present invention does not. The Najarian et al. strain has numerous differences from wild-type HAV HM-175 including an adenine at position 203 and a thymine at the 3' end of the genome. This strain, like the strain of the present invention, also contains a nucleotide difference at position 6522, resulting in an amino acid change from wild-type HAV HM-175 of a serine to a threonine. All of the cell culture adapted HAV stains that have been sequenced in the capsid region have nucleotide differences from wild-type HAV HM-175 at positions 1742 and 2864 that do not result in amino acid changes from the wild-type.

SPECIFIC DISCLOSURE OF THE INVENTION

The present invention is the development of a variant of wild-type HAV HM-175—a variant which is attenuated in primates and useful as a vaccine. The nucleotide sequence of this variant [are] *is* also disclosed (see Table 1). The mutations found in the P2 and P3 regions of the genome, excluding mutations at nucleotide positions at 7032 and 7430, have been shown to include the mutations that confer the attenuation characteristics on the HM-175 strain of HAV. Two nucleotide substitutions resulting in amino acid changes in the HAV protein 2B are quite important for growth in cell culture. In particular, the present invention provides the following:

1. An attenuated hepatitis A virus comprising a genome characterized by the following [nucleotides] *bases*: cytosine at positions 3919, 4043, 4222 and 4810; guanine at positions 964 and 3196; adenine at positions 1742, 2864, 4185, 4563, 5204, 6147 and 6522; and thymine at positions 3025, 3889, 4087 and 5232.

2. An attenuated hepatitis A virus comprising a genome coding for the following amino acids: an arginine is encoded at nucleotide position 964; [valine] *serine* at nucleotide positions 3196, 4222 and 4810; alanine at position 3919; methionine at position 4087; lysine at position 4185; isoleucine at position 4563; tyrosine at position 5232; asparagine at position 6147; and threonine at position 6522.

3. A tissue culture adapted hepatitis A virus comprising a genome characterized by a cytosine at nucleotide position 3919 and a thymine at nucleotide position 3889.

4. A tissue culture adapted hepatitis A virus comprising a genome coding for the following amino acids: an alanine at nucleotide position 3919 and a valine at nucleotide position 3889.

5. A pharmaceutical composition, comprising immunogenic amount of the virus of item 4 above and pharmaceutically acceptable carrier (such as non-toxic, sterile buffer, physiological saline and the like).

6. A method for inducing protective immunity against HAV, comprising administering to a host susceptible to HAV infection, immunogenic amount of the composition of item 5 above, to render said host immune to HAV infection.

Analysis of the nucleotide sequences of wild-type HAV HM-175 and attenuated HM-175/7 indicates that a maximum of 25 nucleotide changes (with 12 amino acid changes) are responsible for cell culture adaptation and attenuation of HAV HM-175. HAV HM-175/7 is different from all other known strains of hepatitis A virus in that it is attenuated in primates, grown in a cell culture, biologically and medically suitable for use as a vaccine.

The clone of the present invention may also contain a cytosine at nucleotide position 4810 (resulting in a serine), a cytosine at 7422 (non-coding), and a thymine at 7479 (non-coding).

HAV HM-175/7 is derived from HM-175/Clone 7, which represents the thirtieth passage of HM-175 in African green monkey kidney cells. HM-175/Clone 7, the master seed, is deposited in the American Type Culture Collection.

FIG. 1 shows the complete nucleotide sequence of wild-type hepatitis A virus, strain [HM-175/7] *HM-175*. Table 1 shows the differences between the nucleotide sequences of wild-type HAV HM-175 and attenuated HAV strain HM-175/7. Comparison of the two sequences shows 25 nucleotide changes distributed throughout the genome.

FIG. 2 shows ligation of cDNA clones to produce full-length wild-type HAV [Hm-175] *HM-175* cDNA. Restriction endonuclease BstXI was used to ligate $pHAV_{LB}228$ (at base 3931 to $pHA_{LB}148$ (at base 3970). The resulting plasmid, pHAV L1, has a 39 base deletion (bases 3931–3970). pHAV L1 was ligated to $pHAV_{LB}24$ at their common ApaI site (base 5687). The resulting plasmid, pHAV L2, was ligated to $pHAV_{L}1307$ at the NcoI site (base 2814) to produce pHAV L3. $pHAV_{L}1688$ was ligated to pHAV L3 at the XbaI site (base 744). The resulting plasmid, pHAV L4, was ligated to $pHAV_{L}r5375$ at the common NcoI site (base 45) to yield pHAV L5. The deletion in pHAV L5 (bases 3931–3970) was repaired by a three-fragment ligation of restriction endonuclease fragments from pHAV L5 (SacI [base 2989]-EcoRI [base 4977]), $pHAV_{LV}288$ (SacI-HincII [] [base 4242]), and $pHAV_{LB}148$ (HincII-EcoRI). The resulting plasmid, pHAV/WT BR322, contains full-length wild-type HAV HM-175 cDNA in plasmid pBR322. Partial restriction endonuclease digests were performed for plasmids $pHAV_{LB}148$ (BstXI), $pHAV_{LB}24$ (ApaI) and pHAV L4 (NcoI). Numbers refer to nucleotide positions in wild-type HAV HM-175 cDNA.

Figure 3:
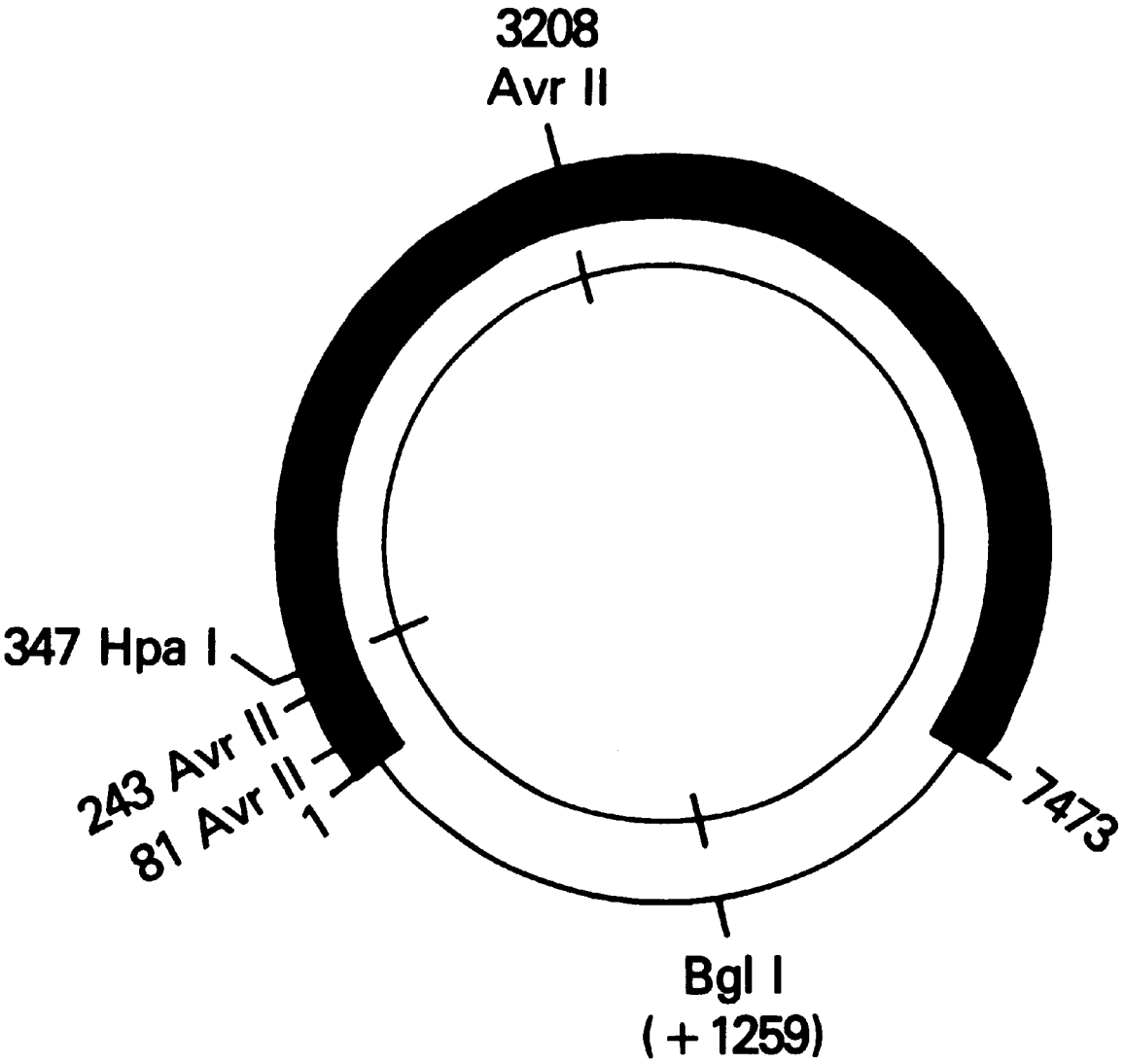

FIG. 3 shows the restriction endonuclease sites common to wild-type and attenuated HAV cDNA used to produce chimeric cDNAs. The solid bar indicates HAV cDNA, and the single line indicates pGEM1 DNA. The inner circle indicates restriction fragments used for ligations. Numbers refer to nucleotide positions in [attenuated] *wild-type* HAV HM-175 cDNA, number in parentheses refers to nucleotide position in PGEM1. AvrII cuts HAV cDNA at three positions; however, only the AVrII site at base 3208 was used to produce restriction fragments.

Figure 4:
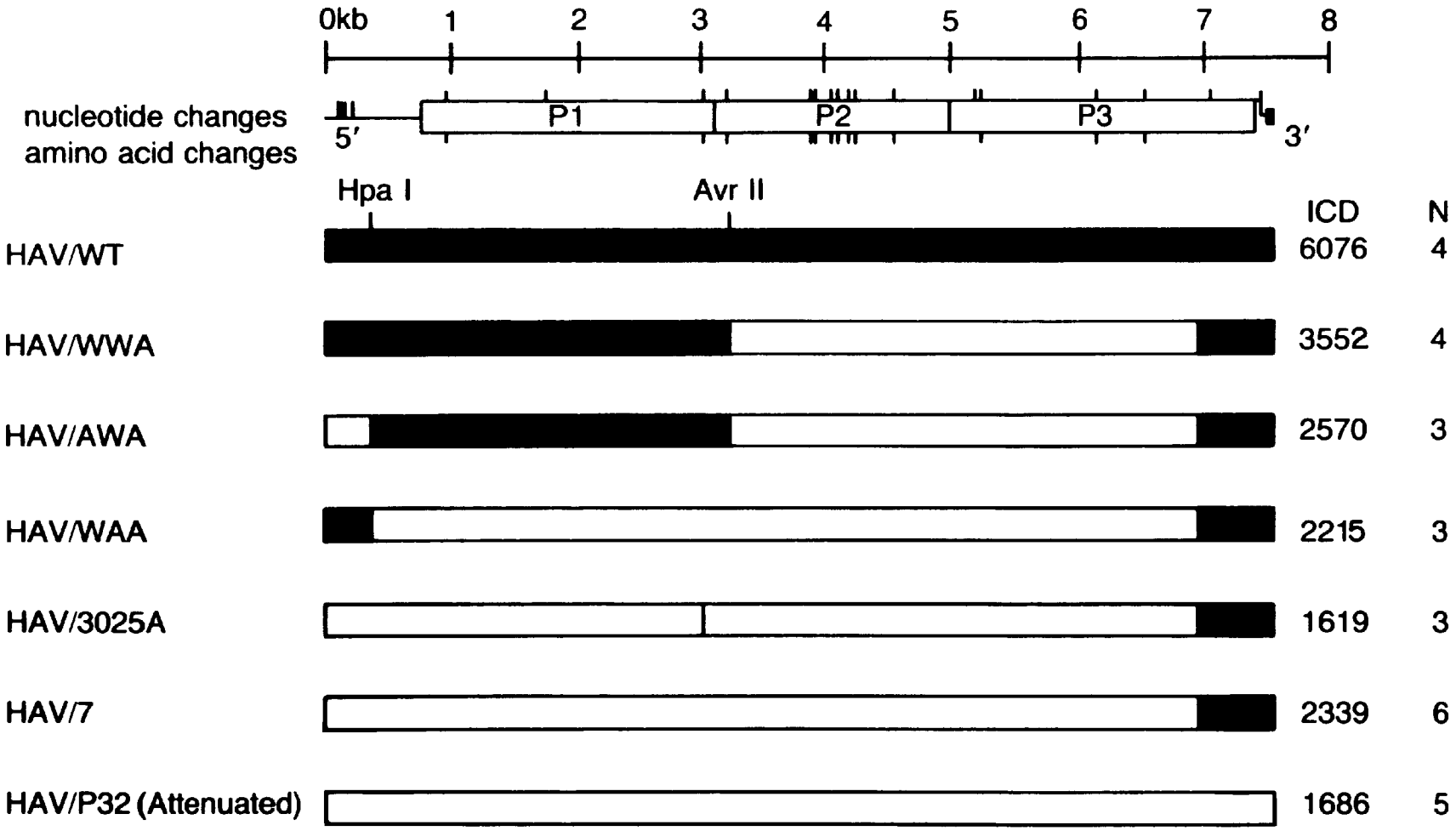

FIG. 4 shows the [Genome] *genome* structure of chimeric HAV cDNAs. The top line shows the length of the HAV genome in kilobases (kb) from the 5' terminus. The second line depicts the genome organization of HAV and the putative gene assignments with nucleotide (and amino acid) differences between wild-type and attenuated HAV HM-175 above (and below) the genome. The genome organization of infectious chimeric viruses is shown with attenuated HAV sequences (open bars) and wild-type sequences (closed bars) along with the restriction endonuclease sites used to divide the cDNAs. HpaI cuts attenuated HAV cDNA at base [347] *355*; all of the nucleotide changes between wild-type and attenuated HAV in the 5' noncoding region are 5' to this site. AvrII cuts attenuated HAV cDNA at base [3208] *3214*; all of the nucleotide changes in the capsid region and one of the nucleotide changes in the gene encoding protein 2A are between the HpaI-AvrII sites. The region of the HAV genome 3' to AvrII contains the nucleotide changes in the P2 regions. Two of the nucleotide changes from wild-type HAV; bases [7027 and 7425] *7032 and 7430*, are not present in any of the chimeric cDNAs. The full-length attenuated HAV genome used to construct the chimeras does not contain these latter two base changes; hence, all of the constructs have wild-type bases at these two positions. ICD indicates geometric mean peak isocitrate dehydrogenase and N indicates number of marmosets inoculated.

Seven nucleotide changes occur in the 5' noncoding region, including 5 base deletions. At nucleotide position 203 to 207, a single thymine (out of 5 consecutive thymines in wild-type HAV) has been deleted in HM-175/7. Seventeen nucleotide changes occur in the amino acid coding region of the genome. Twelve of these base changes result in different amino acids, and seven of these yield amino acids of different charges. Four nucleotide changes occur in the capsid region. The changes in nucleotides 1742 and 2864 do not result in changes in the amino acids. The changes in nucleotide 3025 yields a change in the amino acid sequence of VP1 from glutamic acid in 'wild-type HM-175 to valine in HM-175/7. This is the only amino acid change in the capsid region which results in an amino acid of different charge. One nucleotide change occurs in the 3' noncoding region—an additional thymine at the 3' end of the genome.

Ten amino acid changes between wild-type HAV HM-175 and HM-175/7 occur in proteins 2A, 2B, 2C, 3B and 3D. None of the amino acid changes occur at putative dipeptide cleavage sites or at proposed enzymatic sites of HAV proteins. The nucleotide difference at 6522 changes a serine in protein 3D of wild-type HAV HM-175 to a threonine in HM-175 Pass 35.

Wild type hepatitis A virus (HAV), strain HM-175 was originally recovered from the stool of a patient with hepatitis A and isolated in primary African green monkey kidney (AGMK) cells as is described in Daemer et al., Infect. Immun., 32: 388–393 (1981). The virus was then passaged (up to 26 times) in AGMK cells and then triply cloned by the terminal dilution method. Some of these strains are available from the Americn Type Culture Collection under ATCC designation numbers VR 2089, VR 2090, VR 2091, VR 2092, VR 2093, VR 2097, VR 2098, and VR 2099. The triply cloned variant was then passaged three times in AGMK cells in order to prepare a stock of virus for primate inoculation. This later virus is attenuated for chimpanzees and elicits serum neutralizing antibody. This virus was then passaged three additional times in AGMK cells in order to produce the hepatitis A virus required to perform the cloning and sequence analysis of the present invention, HM-175/7. The entire nucleotide sequence of the genome of this virus is [shown in FIG. 1] *the same as the wild-type sequence shown in FIG. 1 except for the changes from wild-type indicated in Table 1.*

Virus purification and RNA extraction. HAV is purified using a procedure described in Linemeyer et al, J. Virology, 54: 247–255 (1985). Briefly, AGMK cells infected with HAV are trypsinized, pelleted, resuspended in lysis buffer, sonicated twice for three minutes, and incubated on ice for 10 minutes. The sonicated debris is centrifuged at 10,000×g for 20 minutes, the resultant supernatant is centrifuged at 10,000×g for 20 minutes, and the resultant supernatant (from the second centrifugation) is removed and combined with sodium-Sarkosyl (SLS) to 0.5%. The supernatant from the first centrifugation, and pellets from the second and third centrifugation are pooled, resuspended in lysis buffer, and sonicated as above. The sonicated debris is centrifuged twice, as described above, and SLS is added to 0.5%. Both SLS supernatants are pooled, incubated at 37° C. for 30 minutes, and pelleted through a 40% sucrose cushion in lysis buffer for 20 hours at 100,000×g. The pellet is resuspended in 0.5% SLS in TNE, sonicated, and banded in 34% cesium chloride for 60 hours at 100,000×g. Fractions are collected assayed for refractive index, and tested for HAV by radioimmunoassay. The viral peaks are pooled, diluted 40-fold in 0.5% SLS in TNE, and pelleted at 100,000×g overnight. The pellet is resuspended in TNE and HAV RNA is extracted using known techniques. Molecular Cloning. HAV RNA (1.2 $\mu$g), obtained as described above, serves as a template for first-strand [cDMA] *cDNA* synthesis using well known techniques [described, for example, in Ticehurst et al, PNAS USA, 80: 5885–5889 (1983)]. In the preferred embodiment, the concentration of reverse transcriptase is increased to 1,000 U/ml and the reaction is incubated for 45 minutes. The reaction is terminated, RNA-cDNA hybrids are isolated, and second strand cDNA is synthesized using RNase H, E. coli DNA polymerase I, and E. coli DNA ligase. The reaction is terminated and double-stranded (ds) cDNA is isolated. ds cDNA is size selected using a 1 ml Sepharose 4B column. The first four 65 $\mu$l fractions containing ds cDNA are pooled and precipitated in ethanol after the addition of tRNA. Homopolymeric tails of cCMP are added to the ds cDNA using terminal deoxynucleotidyltransferase. The reaction is terminated, phenol extracted, and ethanol precipitated. Plasmid vector pBR322, cleaved at the Pst I site and tailed with dGMP, is hybridized to equimolar amounts of tailed ds cDNA and used to transform E. coli HB101, using standard procedures.

RNA transcripts of hepatitis A virus (HAV) HM-175 cDNA from an attenuated, cell culture-adapted HAV are infectious in cell culture. Cohen et al., J. Virol. 61: 3035–3039. A full-length HAV cDNA from wild-type HAV (propagated in marmosets in vivo) was constructed. Chimeric cDNAs were produced containing portions of both wild-type and attenuated genomes. Oligonucleotide-directed mutagenesis was used to engineer a point mutation into the VP1 gene of attenuated HAV cDNA, so that the sequence of this capsid protein would be identical to that of wild-type virus. Transfection of monkey kidney cells with RNA transcripts from several of the chimeric cDNAs and from the mutagenized cDNA induced production of HAV. Comparison of the growth of attenuated, wild-type, chimeric, and mutant viruses in vitro indicates that the P2–P3 (nonstructural protein) region may be important for cell culture-adaptation of the virus. Inoculation of marmosets with transfection-derived virus also suggests that the P2–P3 region may play an important role in attenuation of HAV HM-175. See FIGS. 2, 3, 4 and Tables 2 and 3. Site directed mutagenesis was also used to individually back mutate the other mutations found in the attenuated pass 35 strain of HM-175 to the sequence of the wild-type. These mutations were tested for their ability to grow in cell culture. When the cytosine at position 3919 and the thymine at position 3889 were back mutated to guanine and cytosine respectively, the virus lost its ability to grow in cell culture.

The vaccine developed from the present invention is suitable for use in mammals or higher primates, including man, chimpanzees, and marmosets. Either triply cloned or twice cloned viral material may be used in the present invention, however, triply cloned viral material is homogeneously superior to the twice cloned virus material for a uniform preparation suitable for a vaccine.

In the preferred embodiment, master seed lots of HAV HM-175 are triply cloned by terminal dilution at passage levels 10, 20 and 30 [Cunningham, A Laboratory Guide in Virology, 5th edition, Burgess Publishing Company, pp. 144–145 (1963)]. The purpose of the dilution is that the highest dilution positive tubes of the procedure originate from a single virus particle, thus providing biological uniformity of the product.

While the strain of the present invention may be produced by cell culture, other methods may be used, for example, in vitro mutagenesis and transfection by cDNA. Furthermore, although the preferred method is propagation in cell culture, the viral genome may be amplified by use of a prokaryotic or eukaryotic vector, or in vivo.

EXAMPLE

In order to analyze the cDNA clones and determine the nucleotide sequence of the HAV genome of the present invention, bacterial clones obtained as described in the Specific Disclosure were transferred to nitrocellulose filters, lysed, and the DNA was bound. Three HAV cDNA probes were prepared corresponding to the middle, 5', and 3' ends of wild-type HAV-cDNA. DNA fragments from plasmids $pHAV_{LB}113$ (Nco I/Xba I digest), $pHAV_{LB}228$ (Pst I digest), and $pHAV_{LB}93$ (Pst I digest) were isolated from agarose gels, nick-translated, and used as probes for hybridization. Approximately 5,000 bacterial clones were screened by colony hybridization to the radiolabeled HAV cDNA clones. The nucleotide sequence of the HAV genome of the present invention was determined directly from plasmid DNA using reverse transcriptase, oligonucleotide primers, and dideoxynucleotide triphosphates, using standard techniques.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

| Nucleotide | Base | | Amino Acid | | Base | | | | |
|---|---|---|---|---|---|---|---|---|---|
| Position | WT | HM-175/7 | WT | HM-175/7 | LA | CR-326 | HM pass 59 | HAS-15 | Italy |
| 124 | T | C(C,C) | | | T | — | T | — | T |
| 131 | T | d(d,d) | | | T | — | T | — | C |
| 132 | T | d(d,d) | | | T | — | T | — | T |
| 133 | T | d(d,d) | | | T | — | T | — | T |
| 134 | G | d(d,d) | | | G | — | G | — | G |
| 152 | A | G(G,G) | | | A | — | A | — | A |
| 203–207 | T | d(d,d) | | | A | — | d | — | — |
| 964 | A | G(G) | Lys | Arg | A | A | A | A | — |
| 1742 | G | A | | | T | C | — | T | — |
| 2864 | T | A(A) | | | G | A | — | A | — |
| 3025 | A | T(T) | Glu | Val | A | A | — | A | — |
| 3196 | A | G(G,G) | Asn | Ser | A | A | — | A | — |
| 3889 | C | T(T,T) | [Alu] *Ala* | Val | C | — | — | C | — |
| 3919 | G | C(C,C) | Gly | Ala | G | — | — | G | — |
| 4043 | T | C(C,C) | | | T | — | — | T | — |
| 4087 | A | T(T,T) | Lys | Met | A | — | — | A | — |
| 4185 | G | A(A) | Glu | Lys | A(Asn) | — | — | A(Asn) | — |
| 4222 | T | C(C) | Phe | Ser | T | — | — | T | — |
| 4563 | G | A(A) | Val | Ile | G | — | — | — | — |
| 4810 | T | C(T,T) | Phe | Ser | T | — | — | — | — |
| 5204 | G | A(A) | | | A | — | — | — | — |
| 5232 | C | T(T) | His | Tyr | C | — | — | — | — |
| 6147 | G | A(A,A) | Asp | Asn | G | — | — | — | — |
| 6522 | T | A(A,A) | Ser | Thr | A(Thr) | — | — | — | — |
| 7032 | T | C(C,C) | | | T | — | — | — | — |
| 7430 | A | G(G,G) | | | A | — | — | — | — |
| 7433 | T | C(T,T) | | | T | — | — | — | — |
| 7479 | A | T(A,A) | | | A | — | — | — | — |

WT = wild-type HM-175
LA = Najarian et al (PNAS l985)
CR-326 = Linemeyer et al (JV l985)
Pass 59 = Ross (JGV 1986)
HAS-15 = Ovchinnikov et al (DANS 1986)
Italy = Venuti et al (JV 1985)
Nucleotide positions correspond to numbering for wild-type HM-175 (Cohen 1986). Bases in parentheses indicate bases sequenced on additional clones, hyphens indicate nucleotide sequences not determined, amino acids in parentheses indicate amino acid differing from wild-type HM-175.
Nucleotide 4810 is a thymine in wild-type HAV HM-175 and two of the three cDNA clones from HM-175/7.
Nucleotide 7433 is T in wild-type HAV HM-175 and two of three cDNA clones from HM-175 Pass 35; the third cDNA clone has a C at base 7433. An additional T is added at the 3' end of the genome in one of three cDNA clones of HM-175 Pass 35.
The nucleotide sequences of the cell culture adapted strains (e.g., LA, [Cr-326] *CR-326*, etc.) differ from wild-type HM-175 in more positions than indicated here; nucleotides listed are only those where wild-type HM-175 differs from HM-175/7.
Citations:
Najarian et al, PNAS, 79; 5793–5797 (1982).
Linemeyer et al., J. Virol., 54-247–255 (1985).
Ross et al, J. Gen. Virol., in press.
[Ovchimmikov] *Ovchinnikov* et al, Doki Akad Nauk SSSR, 285: 1014–1018 (1985).
Cohen et al, "Nucleotide sequence of wild-type hepatitis A virus," in press.

TABLE 2

In vitro and in vivo transfections with HAV cDNA and its RNA transcripts

| Transfection of Secondary AGMK Cells | HAV Produced |
|---|---|
| pHAV/7 RNA | + |
| pHAV/7 RNA | + |
| pHAV/3025A RNA | + |
| pHAV/WAA RNA | + |
| pHAV/WWA RNA | + |
| pHAV/AWA RNA | + |

TABLE 2-continued

In vitro and in vivo transfections with HAV cDNA and its RNA transcripts

| | |
|---|---|
| [pHAV/AAW RNA | –] |
| [pHAV/AAW RNA | –] |
| [pHAV/WAW RNA | –] |
| [pHAV/WT RNA | –] |
| **Intrahepatic Inoculation of Marmosets** | **HAV Seroconversion** |
| pHAV/7 RNA | – |
| pHAV/7 DNA | – |
| [pHAV/AAW; pHAV/AWW] | |
| [pHAV/WAW] | |
| [pooled RNA | –] |
| [pHAV/WT RNA | –] |
| [pHAV/WT DNAep | –] |

TABLE 3

Liver enzymes of marmosets receiving transfection-derived viruses

| Inoculum | Marmoset number | Peak ICD level (sigma units/ml) | Week After Inoculation Until: Peak ICD level | Week After Inoculation Until: Positive anti-HAV antibody |
|---|---|---|---|---|
| HAV/7 | 460 | 3,320 | 9 | 8 |
| | 517 | 2,203 | 10 | 10 |
| HAV/3025A | 501 | 1,419 | 8 | 6 |
| | 506 | 1,315 | 2 | 5 |
| | 534 | 2,276 | 12 | 8 |
| HAV/WAA | 532* | 1,513 | 11 | 11 |
| | 552 | 2,430 | 5 | 3 |
| HAV/AWA | 479 | 8,147 | 7 | 7 |
| | 489 | 1,676 | 7 | 7 |
| | 522 | 1,245 | 9 | 7 |
| HAV/WWA | 525 | 3,265 | 5 | 5 |
| | 526 | 3,173 | 8 | 5 |
| | 528 | 5,298 | 5 | 4 |
| | 529 | 2,904 | 7 | 5 |

*Serum for ICD determination was not obtained four prior to seroconversion for this animal.

What is claimed is:

1. An attenuated hepatitis A virus [comprising a] *whose* genome *has a cDNA sequence according to FIG. 1* [characterized by the following nucleotides: cytosine at] *except for nucleotide* positions 3919, 4043, 4222 and 4810; *which have cytosines as bases;* [guanine at] *nucleotide* positions 964 and 3196 *which have guanines as bases*; [adenine at] *nucleotide* positions 1742, 2864, 4185, 4563, 5204, 6147 and 6522 *which have adenines as bases*; and [thymine at] *nucleotide* positions 3025, 3889, 4087 and 5232 *which have thymines as bases*.

2. The attenuated hepatitis A virus of claim 1 wherein [said genome encodes the following amino acids: an arginine is encoded at nucleotide] *the base change at* position 964 *results in a codon which encodes arginine*; [valine at nucleotide] *the base changes at* positions *3025 and 3889 result in codons which encode valine; the base changes at positions* 3196, 4222 and 4810 *result in codons which encode serine*; [alanine at] *the base change at* position 3919 *results in a codon which encodes an alanine*; [methionine at] *the base change at* position 4087 *results in a codon which encodes a methionine*; [lysine at] *the base change at* position 4185 *results in a codon which encodes a lysine*; [isoleucine at] *the base change at* position 4563 *results in a codon which encodes an isoleucine*; [tyrosine at] *the base change at* position 5232 *results in a codon which encodes a tyrosine*; [asparagine at] *the nucleotide change at* position 6147 *results in a codon which encodes an asparagine*; and [threonine at] *the nucleotide change at* position 6522 *results in a codon which encodes a threonine*.

3. A tissue culture adapted hepatitis A virus [comprising a] *whose* genome *has a cDNA sequence according to FIG. 1* [characterized by a cytosine at] *except for* nucleotide position 3191 *which has cytosine as a base* and [a thymine at] nucleotide position 3889 *which has thymine as a base*.

4. The tissue culture adapted hepatitis A virus of claim 3 wherein [said genome encodes the following amino acids: an alanine at nucleotide] *the base change at* position 3919 *results in a codon which encodes an alanine* and [a valine at nucleotide] *the base change at* position 3889 *results in a codon which encodes a valine*.

5. A pharmaceutical composition, comprising *an* immunogenic amount of the virus of claim 4 and pharmaceutically acceptable carrier.

6. A method for inducing protective immunity against HAV, comprising administering to a host susceptible to HAV infection, immunogenic amount of hepatitis A virus comprising a genome coding for alanine at nucleotide position 3919 and valine at nucleotide position 3889, to render said host immune to HAV infection.

*7. An isolated nucleic acid molecule comprising sequence according to FIG. 1 where said sequence encodes HAV HM-175 wild-type hepatitis A virus.*

*8. A nucleic acid molecule encoding an attenuated hepatitis A virus, said molecule having a nucleotide sequence according to FIG. 1 except for nucleotide positions 3919, 4043, 4222 and 4810 which have cytosines as bases; nucleotide positions 964 and 3196 which have guanines as bases; nucleotide positions 1742, 2864, 4185, 4563, 5204, 6147 and 6522 which have adenines as bases; and nucleotide positions 3025, 3889, 4087 and 5232 which have thymines as bases.*

*9. A nucleic acid molecule encoding an attenuated hepatitis A virus, said molecule having a nucleotide sequence according to FIG. 1 except for nucleotide positions 3919, 4043 and 4222 which have cytosines as bases, nucleotide positions 4185, 4563, 5204, 6147 and 6522 which have adenines as bases; and nucleotide positions 3889, 4087 and 5232 which have thymines as bases.*

*10. A nucleic acid molecule encoding an attenuated hepatitis A virus, said molecule having a nucleotide sequence according to FIG. 1 except for nucleotide positions 3919, 4043 and 4222 which have cytosines as bases; nucleotide positions 1742, 2864, 4185, 4563, 5204, 6147 and 6522 which have adenines as bases; nucleotide positions 3025, 3889, 4087 and 5232 which have thymines as bases, and nucleotide positions 964 and 3196 which have guanines as bases.*

*11. An attenuated hepatitis A virus whose genome has a cDNA sequence according to FIG. 1 except for nucleotide positions 3919, 4043 and 4222 which have cytosines as bases, nucleotide positions 4185, 4563, 5204, 6147 and 6522 which have adenines as bases, and nucleotide positions 3889, 4087 and 5232 which have thymines as bases.*

*12. A vaccine comprising an immunologically effective amount of the virus according to claim 11 in a pharmaceutically acceptable carrier or diluent.*

*13. An attenuated hepatitis A virus whose genome as a cDNA sequence according to FIG. 1 except for nucleotide positions 3919, 4043 and 4222 which have cytosines as bases; nucleotide positions 1742, 2864, 4185, 4563, 5204, 6147 and 6522 which have adenines as bases; nucleotide positions 3025, 3889, 4087 and 5232 which have thymines as bases; and nucleotide positions 964 and 3196 which have guanines as bases.*

*14. A vaccine comprising an immunologically effective amount of the virus according to claim 13 in a pharmaceutically acceptable carrier or diluent.*

*15. A nucleic acid molecule encoding a tissue culture adapted hepatitis A virus, said molecule having a nucleotide sequence according to FIG. 1 except for nucleotide position 3919 which has cytosine as a base and nucleotide position 3889 which has thymine as a base.*

*16. A nucleic acid molecule encoding an attenuated hepatitis A virus, said molecule having a nucleotide sequence according to FIG. 1 except for nucleotide positions 131–134 which are deleted, and nucleotide positions 203–207 from which a single thymine is deleted; nucleotide positions 124, 3919, 4043 and 4222 which have cytosines as bases, nucleotide positions 4185, 4563, 5204, 6147 and 6522 which have adenines as bases; nucleotide positions*

*3889, 4087 and 5232 which have thymines as bases; and nucleotide position 152 which has a guanine as a base.*

*17. An attenuated hepatitis A virus whose genome has a cDNA sequence according to FIG. 1 except for nucleotide positions 131–134 which are deleted, nucleotide positions 203–207 from which a single thymine is deleted; nucleotide positions 124, 3919, 4043 and 4222 which have cytosines as bases, nucleotide positions 4185, 4563, 5204, 6147 and 6522 which have adenines as bases; nucleotide positions 3889, 4087 and 5232 which have thymines as bases; and nucleotide position 142 which has a guanine as a base.*

*18. A vaccine comprising an immunologically effective amount of a virus according to claim 17 in a pharmaceutically acceptable carrier or diluent.*

*19. A nucleic acid molecule encoding an attenuated hepatitis A virus, said molecule having a nucleotide sequence according to FIG. 1 except for nucleotide positions 131–134 which are deleted, at nucleotide positions 203–207 from which a single thymine is deleted; nucleotide positions 124, 3919, 4043 and 4222 which have cytosines as bases; nucleotide positions 1742, 2864, 4185, 4563, 5204, 6147 and 6522 which have adenines as bases; and nucleotide positions 3889, 4087 and 5232 which have thymines as bases, nucleotide positions 152, 964 and 3196 which have guanines as bases.*

*20. An attenuated hepatitis A virus whose genome has a cDNA sequence according to FIG. 1 except for nucleotide positions 131–134 which are deleted, nucleotide positions 203–207 from which a single thymine is deleted; nucleotide positions 124, 3919, 4043 and 4222 which have cytosines as bases; nucleotide positions 1742, 2864, 4185, 4563, 5204, 6147 and 6522 which have adenines as bases; nucleotide positions 3889, 4087 and 5232 which have thymines as bases; nucleotide positions 152, 964 and 3196 which have guanine as bases.*

*21. A vaccine comprising an immunologically effective amount of a virus according to claim 20 in a pharmaceutically acceptable carrier or diluent.*

*22. An attenuated hepatitis A virus whose genome has a cDNA sequence according to FIG. 1 except for nucleotide positions 3919, 4043 and 4222 which have cytosines as bases; nucleotide positions 964 and 3196 which have guanines as bases; nucleotide positions 1742, 2864, 4185, 4563, 5204, 6147 and 6522 which have adenines as bases; nucleotide positions 3025, 3889, 4087 and 5232 which have thymines as bases.*

*23. The attenuated hepatitis A virus of claim 22 wherein the base change at position 964 results in a codon which encodes arginine; the base changes at positions 3025 and 3889 result in codons which encode valine; the base changes at positions 3196 and 4222 result in codons which encode serine; the base change at position 3919 results in a codon which encodes an alanine; the base change at position 4087 results in a codon which encodes a methionine; the base change at position 4185 results in a codon which encodes a lysine; the base change at position 4563 results in a codon which encodes an isoleucine; the base change at position 5232 results in a codon which encodes a tyrosine; the base change at position 6147 results in a codon which encodes an asparagine; and the base change at position 6522 results in a codon which encodes a threonine.*

*24. A nucleic acid molecule encoding an attenuated hepatitis A virus, said molecule having a nucleotide sequence according to FIG. 1 except for nucleotide positions 3919, 4043 and 4222 which have cytosines as bases; nucleotide positions 964 and 3196 which have guanines as bases; nucleotide positions 1742, 2864, 4185, 4563, 5204, 6147 and 6522 which have adenines as bases; nucleotide positions 3025, 3889, 4087 and 5232 which have thymines as bases.*

* * * * *